(12) United States Patent
Masson et al.

(10) Patent No.: US 9,101,413 B2
(45) Date of Patent: Aug. 11, 2015

(54) POP ON SPREADER SYSTEM

(71) Applicant: DePuy Synthes Products, Inc., Raynham, MA (US)

(72) Inventors: Robert Masson, Windermere, FL (US); Kenneth R. Underhill, West Chester, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 30 days.

(21) Appl. No.: 13/652,920

(22) Filed: Oct. 16, 2012

(65) Prior Publication Data

US 2014/0107656 A1    Apr. 17, 2014

(51) Int. Cl.
| A61B 17/66 | (2006.01) |
| A61B 17/70 | (2006.01) |
| A61B 17/02 | (2006.01) |
| A61B 17/60 | (2006.01) |

(52) U.S. Cl.
CPC ........... *A61B 17/7077* (2013.01); *A61B 17/025* (2013.01); *A61B 17/66* (2013.01); *A61B 2017/0256* (2013.01); *A61B 2017/606* (2013.01)

(58) Field of Classification Search
CPC ...... A61B 17/025; A61B 17/60; A61B 17/66; A61B 17/7077; A61B 2017/0256; A61B 2017/606
USPC ............. 606/57–58, 86 A, 86 R, 90, 105, 914
See application file for complete search history.

(56) References Cited

U.S. PATENT DOCUMENTS

| 4,826,144 | A | | 5/1989 | Balsells |
| 4,915,366 | A | | 4/1990 | Balsells |
| 4,974,821 | A | | 12/1990 | Balsells |
| 5,082,390 | A | * | 1/1992 | Balsells ................. 403/326 |
| 5,108,078 | A | | 4/1992 | Balsells |
| 5,139,276 | A | | 8/1992 | Balsells |
| 5,411,348 | A | | 5/1995 | Balsells |
| 6,648,891 | B2 | * | 11/2003 | Kim ......................... 606/86 B |
| 7,175,441 | B2 | | 2/2007 | Naviaux et al. |
| 7,578,822 | B2 | * | 8/2009 | Rezach et al. ............... 606/90 |
| 7,758,584 | B2 | | 7/2010 | Bankoski et al. |
| 7,918,792 | B2 | | 4/2011 | Drzyzga et al. |
| 7,942,909 | B2 | | 5/2011 | Hammill, Sr. et al. |
| 8,075,603 | B2 | | 12/2011 | Hammill, Sr. et al. |
| 8,197,518 | B2 | | 6/2012 | Hammill, Sr. et al. |

(Continued)

FOREIGN PATENT DOCUMENTS

| FR | 2821543 | 9/2002 |
| WO | WO 2005/009209 | 2/2005 |
| WO | WO 2012/074803 | 6/2012 |

*Primary Examiner* — Larry E Waggle, Jr.
(74) *Attorney, Agent, or Firm* — Baker & Hostetler LLP (57) ABSTRACT

A post that is configured to be coupled to a head of a bone fixation element that is attached to a bone part can include a post body that is elongate along a first direction and defines a proximal end and a distal end that is spaced from the proximal end along the first direction. The post body can include an internal surface that defines a socket at the distal end. The socket can be configured to receive the head of the bone fixation element. The post can further include a locking member that is disposed within the socket such that when the socket receives the head of the bone fixation element the locking member couples the post body to the bone fixation element. The post body is polyaxially pivotable relative to the head when the post body is coupled to the bone fixation element.

13 Claims, 5 Drawing Sheets

(56) References Cited

U.S. PATENT DOCUMENTS

| | | | |
|---|---|---|---|
| 8,834,485 B2* | 9/2014 | Kave | 606/102 |
| 2003/0055430 A1 | 3/2003 | Kim | |
| 2003/0204262 A1 | 10/2003 | Ferguson et al. | |
| 2005/0203533 A1* | 9/2005 | Ferguson et al. | 606/90 |
| 2009/0287212 A1* | 11/2009 | Hirata et al. | 606/59 |
| 2010/0217088 A1 | 8/2010 | Heiges et al. | |
| 2010/0268284 A1 | 10/2010 | Bankoski et al. | |
| 2010/0331849 A1 | 12/2010 | Riesinger et al. | |
| 2011/0130634 A1 | 6/2011 | Solitario, Jr. et al. | |
| 2011/0130793 A1 | 6/2011 | Woolley et al. | |
| 2012/0203279 A1 | 8/2012 | Walters et al. | |

* cited by examiner

POP ON SPREADER SYSTEM

BACKGROUND

Spinal surgery often requires removal of the existing intervertebral disc tissue located between adjacent vertebrae and replacement thereof with an intervertebral implant which may take the form of a cage or other fusion device or an artificial disc which may be of the type which allows limited universal movement of the adjacent vertebrae with respect to each other.

It may be desired to initially separate the adjacent vertebrae from each other and to retain them apart, prior to cleaning out the existing disc tissue and inserting the intervertebral implant. To distract adjacent vertebrae away from each other, an instrument having a pair of anchor screws, one anchored in each of the adjacent vertebrae, is typically used to move the vertebrae apart.

SUMMARY

In an embodiment, a spreader system can include a first post configured to be coupled to a first bone fixation element and a second post configured to be coupled to a second bone fixation element that is attached to a second bone part. The first post can include a first post body that is elongate along a first direction and defines a proximal end and a distal end spaced from the proximal end along the first direction. The first post can further include a first socket that extends into the distal end of the first post body and a first expandable member disposed within the first socket such that as the first socket receives a head of the first bone fixation element the first expandable member expands to permit the first socket to receive the head, and after the first socket has received the head the first expandable member contracts to thereby couple the first bone fixation element to the first post such that the first post is poly-axially pivotable relative to the head of the first bone fixation element. At least one of the first post and second post is configured to move relative to the other after the first and second posts have been coupled to the first and second bone fixation elements, respectively.

In another embodiment, a post that is configured to be coupled to a head of a bone fixation element that is attached to a bone part can include a post body that is elongate along a first direction and defines a proximal end and a distal end that is spaced from the proximal end along the first direction. The post body can include an internal surface that defines a socket at the distal end. The socket can be configured to receive the head of the bone fixation element. The post can further include a coil spring that is disposed within the socket such that when the socket receives the head of the bone fixation element the coil spring couples the post body to the bone fixation element. The post body is polyaxially pivotable relative to the head when the post body is coupled to the bone fixation element.

In another embodiment, a method of spreading anatomical structures can include the steps of attaching a first bone fixation element to a first bone part, the first bone fixation element having a first head; attaching a second bone fixation element to a second bone part, the second bone fixation element having a second head; coupling a first post to the first head by moving the first post toward the first head, wherein the first post is polyaxially pivotable relative to the first head when the first post is coupled to the first head; and coupling a second post to the second head by moving the second post toward the second head, wherein the second post is polyaxially pivotable relative to the second head when the second post is coupled to the second head.

BRIEF DESCRIPTION OF THE DRAWINGS

The foregoing summary, as well as the following detailed description of illustrative embodiments of spreader system of the present application, will be better understood when read in conjunction with the appended drawings. For the purposes of illustrating the spreader system of the present application, there is shown in the drawings illustrative embodiments. It should be understood, however, that the application is not limited to the precise arrangements and instrumentalities shown. In the drawings.

DETAILED DESCRIPTION

Certain terminology is used in the following description for convenience only and is not limiting. The words "right", "left", "lower" and "upper" designate directions in the drawings to which reference is made. The words "inner" or "distal" and "outer" or "proximal" refer to directions toward and away from, respectively, the geometric center of the implant and related parts thereof The words, "anterior", "posterior", "superior," "inferior," "medial," "lateral," and related words and/or phrases are used to designate various positions and orientations in the human body to which reference is made and are not meant to be limiting. The terminology includes the above-listed words, derivatives thereof and words of similar import.

Figure 1:
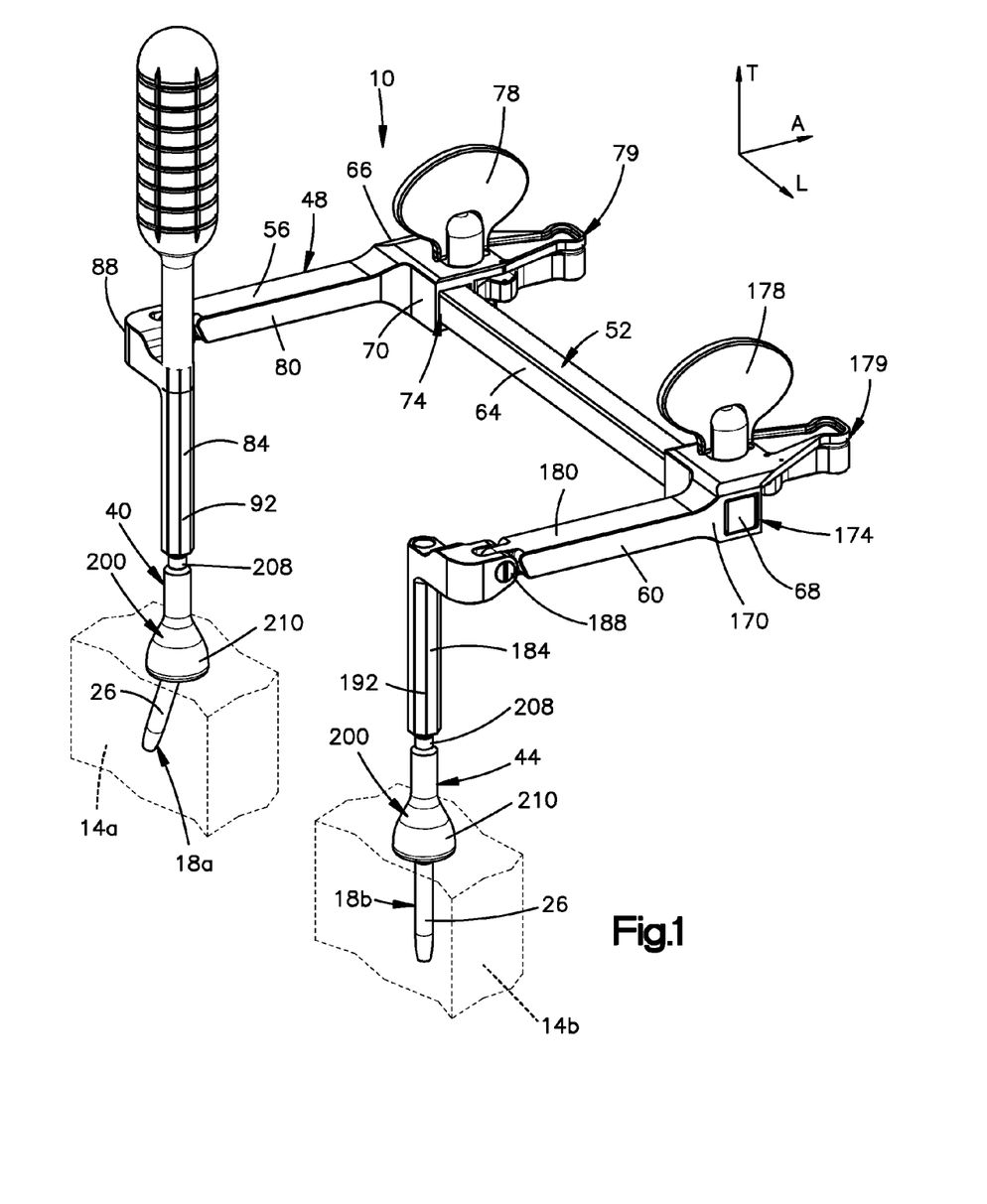
FIG. 1 is a perspective view of a spreader system in accordance with an embodiment, the spreader system including a first post coupled to a head of a first bone fixation element, a second post coupled to a head of a second bone fixation element, and a distractor device having a first arm coupled to the first post, a second arm coupled to the second post, and a connecting member configured to cause at least one of the first and second posts to pivot relative to the bone fixation element.

Referring to FIG. 1, a spreader system configured as a distractor 10 is configured to be coupled to a first bone part 14a and a second bone part 14b such that the distractor 10 is configured to move at least one of the first and second bone parts 14a and 14b relative to the other. As shown in FIG. 1, a first bone fixation element 18a can be attached to the first bone part 14a and a second bone fixation element 18b can be attached to the second bone part 14b. Each bone fixation element 18a and 18b includes a head 22 and a shaft 26 that extends from the head 22. The shafts 26 are configured to engage bone to thereby couple the bone fixation elements 18a and 18b to the first and second bone parts 14a and 14b. The distractor 10 is configured to be coupled to the heads 22 of the first and second bone parts 14a and 14b to thereby couple the distractor 10 to the first and second bone parts 14a and 14b.

Each head 22 of the bone fixation elements 18a and 18b can include a curved surface 19 that extends out from the shaft 26 such that the diameter of head 22 increases as the head extends proximally from the shaft 26. The curved surface 19 can be substantially spherical as illustrated. It should be appreciated, however, that the curved surface 19 can have any configuration as desired. For example, the curved surface can be coned shaped.

The distractor 10 is described herein as extending horizontally along a longitudinal direction "L" and lateral direction "A", and vertically along a transverse direction "T". Unless otherwise specified herein, the terms "lateral," "longitudinal," and "transverse" are used to describe the orthogonal directional components of various components. It should be appreciated that while the longitudinal and lateral directions are illustrated as extending along a horizontal plane, and that the transverse direction is illustrated as extending along a vertical plane, the planes that encompass the various directions may differ during use. For instance, when the spreader system is coupled to first and second vertebrae, the transverse direction T may extend vertically generally along the anterior-posterior direction, while the horizontal plane defined by the longitudinal direction L and lateral direction A lies generally in the anatomical plane defined caudal-cranial direction and the medial-lateral direction, respectively. Accordingly, the directional terms "vertical" and "horizontal" are used to describe the distractor 10 and its components as illustrated merely for the purposes of clarity and illustration.

As shown in FIG. 1, the distractor 10 can include a first post 40 configured to extend through tissue and be coupled to the head 22 of the first bone fixation element 18a, a second post 44 configured to extend through tissue and be coupled to the head 22 of the second bone fixation element 18b, and a spreader device such as a distractor device 48 that is configured to couple to the first and second posts 40 and 44 such that the distractor device 48 can move at least one of the first and second posts 40 and 44 relative to the other so as to move at least one of the first and second bone parts 14a and 14b relative to the other. The first and second posts 40 and 44 are configured to couple to the heads 22 of the first and second bone fixation elements 18a and 18b such that the first and second posts 40 and 44 are polyaxially pivotal relative to the heads 22 of the first and second bone fixation elements 18a and 18b, respectively.

With continued reference to FIG. 1, the distractor device 48 includes a frame 52 having a first arm 56, a second arm 60, and a connecting member 64 that couples the first arm 56 to the second arm 60 such that at least one of the first and second arms 56 and 60 is configured to move relative to the other along the connecting member 64. In particular, the first arm 56 is configured to couple to the first post 40 and the second arm 60 is configured to couple to the second post 44 such that as at least one of the first and second arms 56 and 60 is moved relative to the other, at least one of the first and second posts 40 and 44 is moved relative to the other.

As shown in FIG. 1, the connecting member 64 is elongate along the longitudinal direction L and defines a first end 66 and a second end 68 that is spaced from the first end 66 along the longitudinal direction L. The connecting member 64 can be block shaped and substantially smooth such that the first and second arms 56 and 60 are capable of sliding along the connecting member 64 toward each other and toward respective ends 66 and 68. It should be appreciated, however, that connecting member 64 can have any shape as desired. For example, the connecting member 64 can be cylindrical and can have ratchet teeth such that the first and second arms 56 and 60 can be moved along the connecting member 64 using a ratchet mechanism.

Figure 2A:
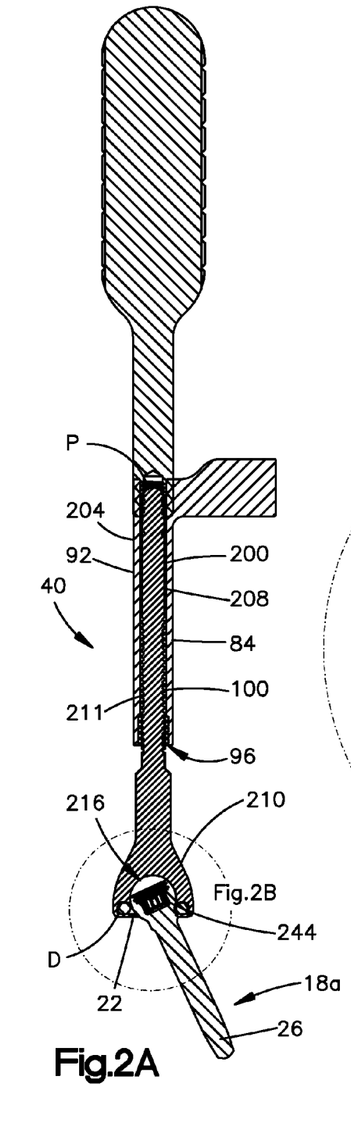
FIG. 2A is a cross-sectional view of the first post shown in FIG. 1, the first post including a first post body, a socket extending into an end of the first post body, and a locking member disposed within the socket.

As shown in FIGS. 1 and 2A, the first arm 56 and the second arm 60 can be moveably coupled to the connecting member 64 such that the arms 56 and 60 can move toward and away from each other along the connecting member 64. As shown, the first arm 56 includes a first mount 70 that defines a first channel 74 that extends through the mount 70 along the longitudinal direction L. The first channel 74 is configured to receive the connecting member 64 such that the connecting member 64 is capable of moving through the first channel 74. The first mount 70 further includes a first activation mechanism 78 that is configured to selectively move the first arm 56 along the connecting member 64. In the illustrated embodiment, the first activation mechanism 78 is a knob that is configured such that rotation of the knob moves the first arm 56 along the connecting member 64. It should be appreciated, however, that the first activation mechanism 78 can have any configuration as desired. For example, the activation mechanism 78 can be configured as a clamp that is loosed to allow the first arm to slide along the connecting member 64.

As shown in FIG. 1, the first mount 70 further includes a locking mechanism 79 that is configured to selectively lock the direction in which the first arm 56 can move along the connecting member 64. For example, the locking mechanism 79 is configured to have a first position whereby the first arm 56 is prevented from moving toward the second arm 60, a second position whereby the first arm 56 is prevented from moving away from the second arm 60, and a neutral position, whereby the first arm 56 is free to move along the connecting member 64 either toward or away from the second arm 60. The locking mechanism 79 can be interchanged between the first position, the second position, and the neutral position by pivoting the locking mechanism relative to the first arm 56. The locking mechanism 79 is illustrated in FIG. 1 as being in the neutral position.

As shown in FIG. 1, the first arm 56 further includes a first extension member 80 that extends from the first mount 70 along the lateral direction A, and a first coupling member 84 that is pivotally coupled to an end of the first extension member 80 at a pivot 88. As shown, the first coupling member 84 includes an elongate tube 92 that can pivot about the pivot 88 between a storing position and an operating position. When in the storing position, the elongate tube 92 extends along the lateral direction A and is substantially parallel to the first extension member 80, and when in the operating position, the elongate tube 92 extends along the transverse direction T and is substantially perpendicular to the first extension member 80.

As shown in FIG. 2A, the elongate tube 92 defines a channel 96 that carries a plurality of ridges 100. The channel 96 is configured to receive the first post 40 to thereby couple the first post 40 to the first arm 56. In particular, the first post 40 can include a plurality of ridges that are configured to mate with the ridges 100 to thereby couple the first post 40 to the first coupling member 84 or otherwise to the first arm 56. In particular, the first post 40 loosely rests within the channel 96 and when a radial load is applied to the first arm 56 or first post 40 the ridges 100 engage the ridges of the first post 40 to thereby couple the first post 40 to the first arm 56. It should be appreciated, however, that the first coupling member 84 can include any configuration capable of coupling the first post 40 to the first arm 56. For example, the first coupling member 84 can include deflectable fingers that engage recesses defined by the first post 40. Further, it should be appreciated, that the first post 40 can be rigidly coupled to the first arm 56, as desired and is not limited to being loosely coupled.

With continued reference to FIG. 1, the second arm 60 is substantially similar to the first arm 56 and includes similar features unless otherwise described. As shown, the second arm 60 includes a second mount 170 that defines a second channel 174 that extends through the mount 170 along the longitudinal direction. The second channel 174 is configured to receive the connecting member 64 such that the connecting member 64 is capable of moving through the second channel 174. The second mount 170 further includes a second activation mechanism 178 that is configured to selectively move the second arm 60 along the connecting member 64. In the illustrated embodiment, the second activation mechanism 178 is a knob that is configured such that rotation of the knob moves the second arm 60 along the connecting member 64.

As shown in FIG. 1, the second mount 170 further includes a locking mechanism 179 that is configured to selectively lock the direction in which the second arm 60 can move along the connecting member 64. For example, the locking mechanism 179 is configured to have a first position whereby the second arm 60 is prevented from moving toward the first arm 56, a second position whereby the second arm 60 is prevented from moving away from the first arm 56, and a neutral position, whereby the second arm 60 is free to move along the connecting member 64 either toward or away from the first arm 56. The locking mechanism 179 can be interchanged between the first position, the second position, and the neutral position by pivoting the locking mechanism relative to the second arm 60. The locking mechanism 179 is illustrated in FIG. 1 as being in the neutral position.

The second arm 60 further includes a second extension member 180 that extends from the second mount 170 along the lateral direction A, and a second coupling member 184 that is pivotally coupled to an end of the second extension member 180 at a pivot 188. As shown, the second coupling member 184 includes an elongate tube 192 that can pivot about the pivot 188 between a storing position and an operating position. When in the storing position, the elongate tube 192 extends along the lateral direction A and is substantially parallel to the second extension member 180, and when in the operating position, the elongate tube 192 extends along the transverse direction T and is substantially perpendicular to the second extension member 180.

Similar to the elongate tube 92, the elongate tube 192 defines a channel that carries a plurality of ridges. The channel of the elongate tube 192 is configured to receive the second post 44 to thereby couple the second post 44 to the second arm 60. In particular, the second post 44 can include a plurality of ridges that are configured to mate with the ridges of the elongate tube 192 to thereby couple the second post 44 to the second coupling member 184 or otherwise to the second arm 60.

Figure 2B:
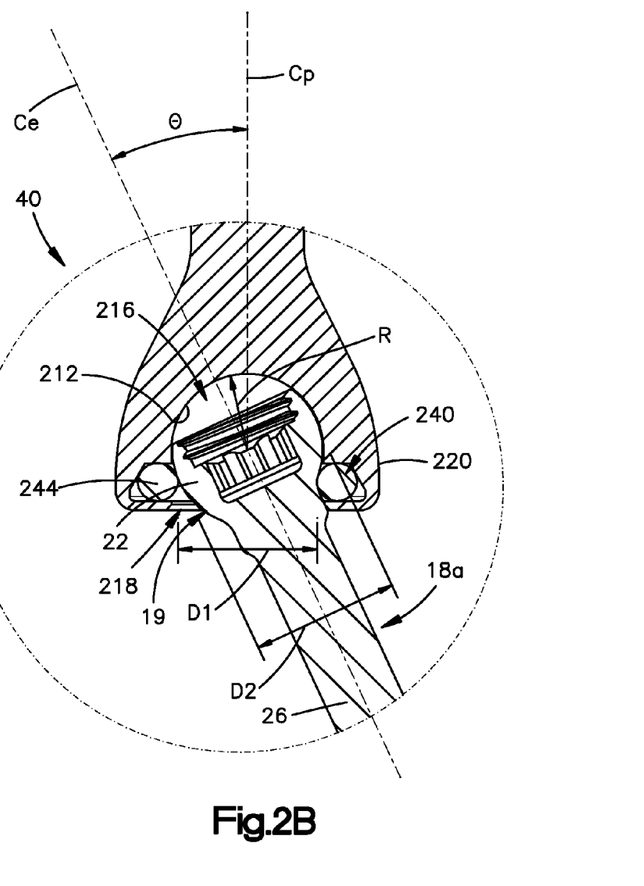
FIG. 2B is a detailed view of the socket of the first post shown in FIG. 2A, the socket being configured to receive the head of the first bone fixation element such that the first post is polyaxially pivotable relative to the head when the first post is coupled to the first bone fixation element.

Now in reference to FIGS. 1, 2A, and 2B, the first and second posts 40 and 44 are configured to couple to the heads 22 of the first and second bone fixation elements 18a and 18b such that the first and second posts 40 and 44 are polyaxially pivotable relative to the heads 22. For example, the first and second posts 40 and 44 are configured to couple to the heads 22 of the first and second bone fixation elements 18a and 18b such that the first and second posts 40 and 44 are polyaxially pivotable relative to the heads 22 in multiple planes such as at least two planes. Each plane can extend at least in the transverse direction T and the planes can be angularly offset with respect to each other such as perpendicular to each other. It can also be said that each post 40 and 44 defines a central axis $C_p$, and each bone fixation element 18a and 18b defines a central axis $C_e$, and that the posts 40 and 44 are polyaxially pivotable relative to the heads 22 such that the central axes $C_p$ of the posts 40 and 44 can be angularly offset with respect to the central axes $C_e$ of the fixation elements 18a and 18b, respectively, by an angle Ø. The angle Ø can be any angle between about $-50°$ and about $50°$ and in some cases between about $-25°$ and about $25°$. It should be appreciated, however, that the posts 40 and 44 can pivot relative to the head between any desired ranges of angles Ø.

The posts 40 and 44 can also be coupled to the heads 22 of the bone fixation elements 18a and 18b such that the posts 40 and 44 are configured to rotate relative to the heads 22 about their respective central axes $C_p$. Therefore the posts 40 and 44 can be both polyaxially pivotable and rotatable relative to the heads 22 of the bone fixation elements 18a and 18b. It should be appreciated, however, that in some embodiments the posts 40 and 44 can be rotatably fixed and/or pivotably fixed relative to the heads 22.

As shown in FIGS. 1, 2A, and 2B, the first post 40 includes a first post body 200 that is elongate along a first direction and defines a proximal end P and a distal end D that is spaced from the proximal end P along the first direction. The first post body 200 includes an engagement member 204 that defines a shaft 208, and a coupling member 210 that extends from a distal end of the engagement member 204. As shown in FIG. 2A, the shaft 208 can carry a plurality of ridges 211 that are configured to mate with the ridges 100 of the elongate tube 92 to thereby couple the first post 40 to the first arm 56. It should be appreciated, however, that the engagement member 204 can have any configuration as desired so long as the first post 40 is capable of extending from the first arm 56. For example, the first post 40 can be integrally formed with the first arm 56

As shown in FIG. 2A, the first post body 200 can include an internal surface 212 that defines a socket 216 at the distal end of the first post body 200, and an opening 218 at the distal end of the first post body 200 that leads into the socket 216. That is, the first post 40 can include a socket 216 that extends into the distal end of the first post body 200. The socket 216 is configured to receive the head 22 of the first bone fixation element 18a through the opening 218 when the first post 40 is moved toward the head 22. As shown in FIG. 2B, the internal surface 212 is substantially spherical and can define a curvature along a first direction that has a first radius r and a second curvature along a second direction that is substantially perpendicular to the first direction that has a second radius r that is substantially equal to the first radius. It should be appreciated, however, that the internal surface 212 can have other shapes as desired. For example, the first and second curvatures can have different radii. The spherical or otherwise curved shaped of the internal surface 212 provides a surface that corresponds to the surface 19 of the head 22 of the first bone fixation element 18a such that the surface 19 can slide along the surface 212 as the first post 40 pivots about the head 22.

As shown in FIG. 2B, the first post body 200 can further include a circumferential recess 220 that extends radially into the internal surface 212 proximate to the opening 218. The recess 220 can be continuous or segmented as desired.

As shown in FIGS. 2A and 2B, the first post 40 can further include a locking member 240 that is disposed within the socket such that when the socket 216 receives the head 22 of the bone fixation element 18a, the locking member 240 couples the first post body 200 to the bone fixation element 18a. In the illustrated embodiment, the locking member 240 is an expandable member 244 that is at least partially disposed within the recess 220. The recess 220 and the expandable member 244 are configured such that as the socket 216 receives the head 22 of the bone fixation element 18a the expandable member 244 expands to an expanded position so as to permit the head 22 to be received within the socket 216, and when the head 22 is received by the socket 216 the expandable member 244 contracts to a holding position to thereby couple the bone fixation element 18a to the post body 200. In particular, the expandable member 244 defines an internal dimension such as a diameter D1. When in the expanded position, the diameter $D_1$ is substantially equal to maximum dimension $D_2$ or diameter of the head 22, and when in the holding position the diameter $D_1$ is less than the maximum dimension $D_2$ to thereby couple the post 40 to the head 22. The expandable member 244 can be configured to provide both a radial load and an axial load to the head 22 of the bone fixation element 18a to thereby retain the head 22 within the socket 216. The expandable member 244 can be a canted-coil spring as illustrated, or the expandable member 244 can be any member capable of expanding when the head 22 is being received by the socket 216. For example, the expandable member 244 can be a rubber washer. Moreover, it should be appreciated, that the locking member 240 can include any structure as desired and is not limited to expandable members. For example, the locking member 240 can be a latch that engages a corresponding latch on the head.

As shown in FIG. 1, the second post 44 is substantially identical to the first post 40 and includes like structure and functions in a similar manner. Therefore, it should be appreciated, that the second post 44 includes all of the features and structure of the first post 40 as shown and described with respect to FIGS. 2A and 2B. It should be further appreciated, however, that while the first and second posts 40 and 44 are illustrated as being identical that in some embodiments the first and second posts 40 and 44 can have certain structures that are different.

In operation, the first bone fixation element 18a can be attached to the first bone part 14a and the second bone fixation element 18b can be attached to the second bone part 14b. The first and second posts 40 and 44 can then be moved through tissue and toward the heads 22 of the first and second bone fixation elements 18a and 18b. Once the distal ends of the first and second posts 40 and 44 contact the heads 22, further movement toward the heads 22 will cause the expandable members 244 to expand and the heads 22 to be received within the sockets 216. When the heads 22 are received within the sockets 216 the expandable members 244 will contract to thereby apply axial and radial loads to the surfaces 19 of the heads 22 and subsequently couple the posts 40 and 44 to the bone fixation elements 18a and 18b. In this way, the posts 40 and 44 can be said to be pop-on or snap-on coupleable. Once the posts 40 and 44 are coupled to the anchors, the distractor device 48 can be moved toward the posts until the posts 40 and 44 are received by the elongate tubes 92 and 192 of the device 48. After the distractor system 10 is coupled to the bone fixation elements 18a and 18b, movement of the arms 56 and 60 along the connecting member 64 will cause at least one of the first and second bone pars 14a and 14b to move relative to the other. After the surgical procedure has been performed, the distractor system 10 can be removed by moving the system 10 away from the heads 22. For example, the distractor device 48 can be first removed, and the posts 40 and 44 can then be subsequently removed. In the illustrated embodiment, as the force away from the heads 22 is increased, the expandable members 244 will once again expand to thereby allow the heads 22 to disengage from the sockets 216. It should be appreciated, that the first and second posts 40 and 44 can be coupled to the distractor device 48 prior to the posts being coupled to the heads 22. It should be further appreciated, that while the distractor system 10 is described as being configured to move bone parts, the system 10 can also be configured to spread tissue.

Figure 3A:
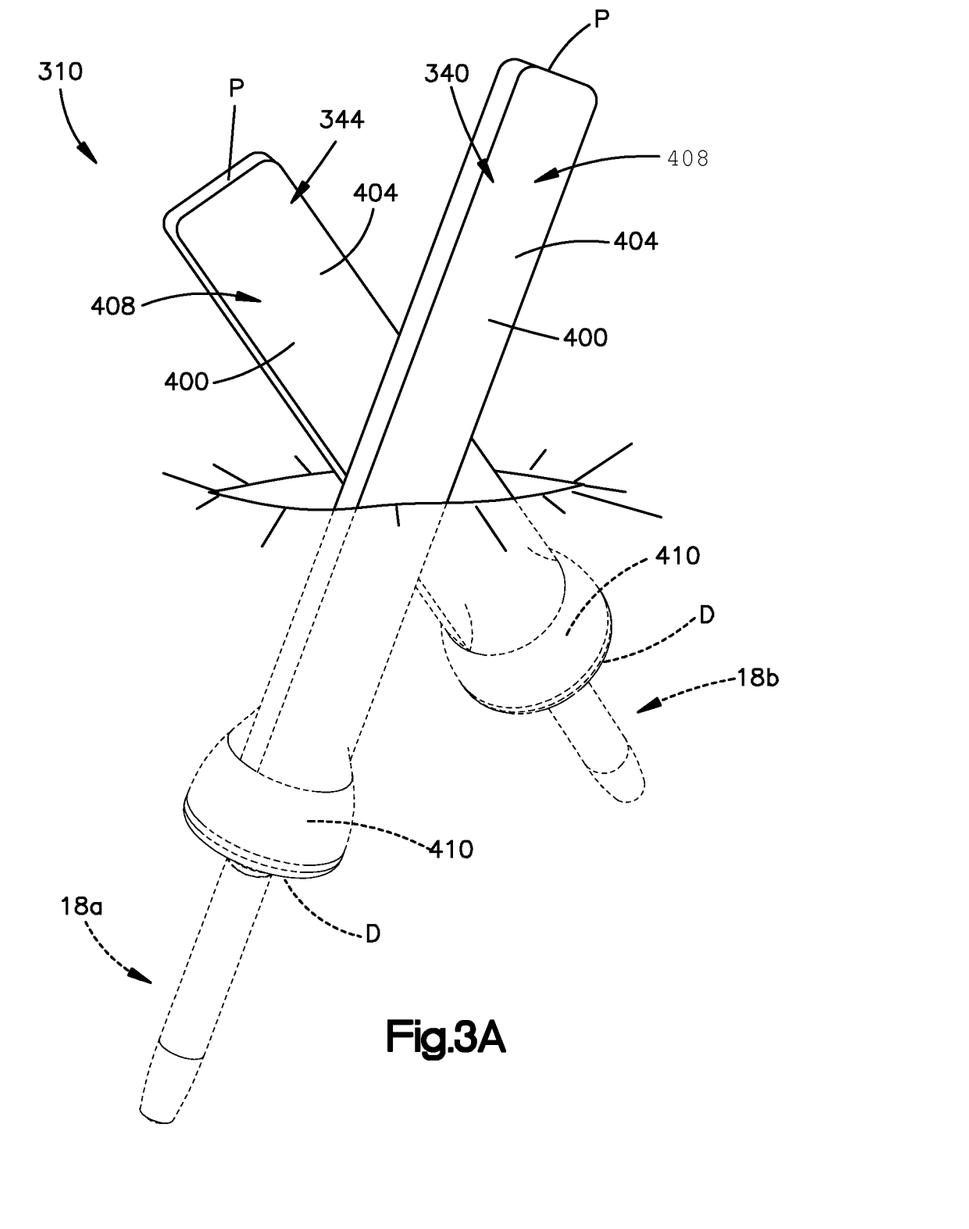
FIG. 3A is a perspective view of a spreader system in accordance with another embodiment, the spreader system including a first post coupled to a head of a first bone fixation element and a second post coupled to a head of a second bone fixation element, at least one of the first and second posts being configured to move away from the other to thereby spread tissue apart.
Figure 3B:
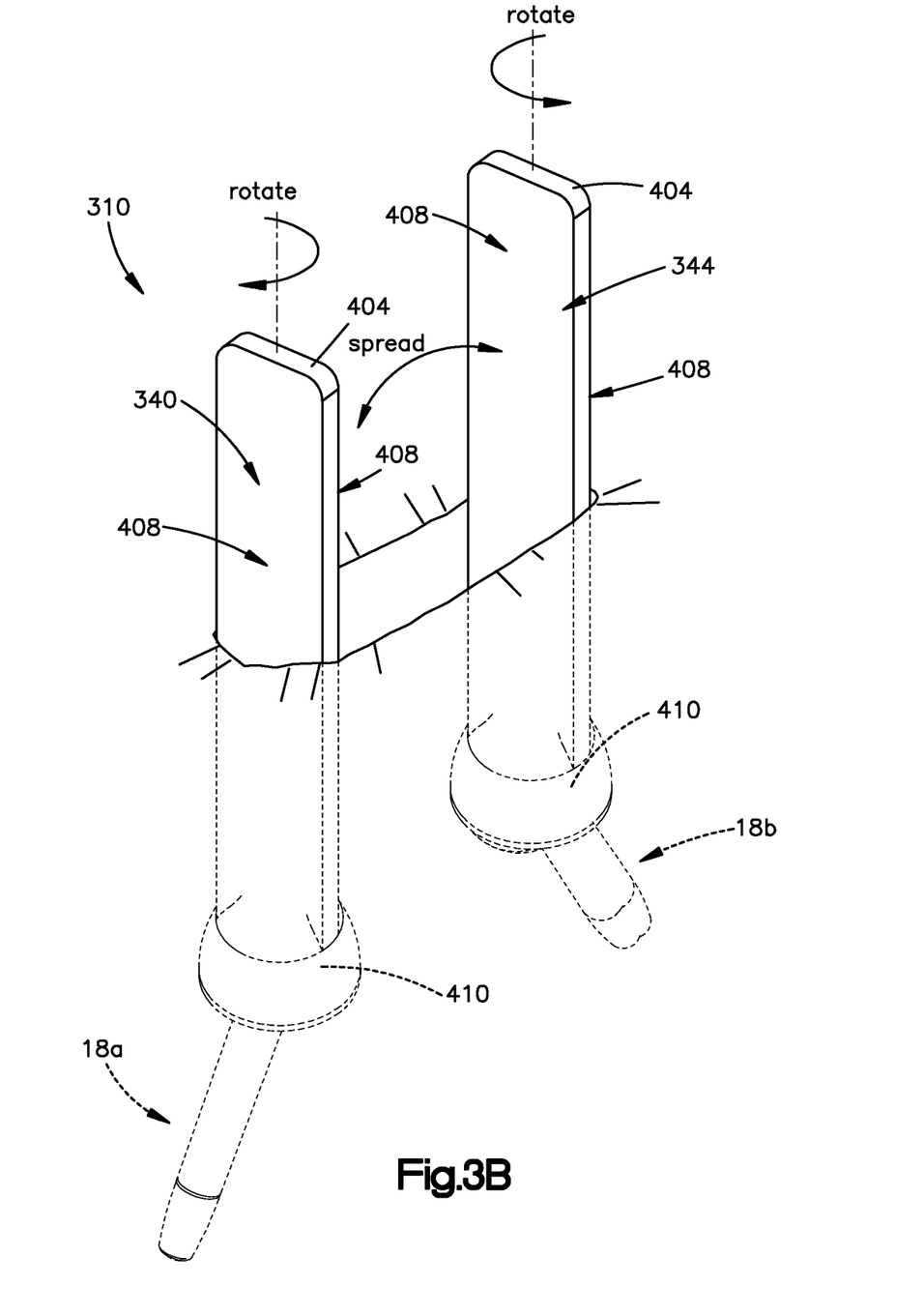
FIG. 3B is a perspective view of the spreader system shown in FIG. 3A, with the first and second posts moved so as to spread tissue to thereby provide a surgical access path.
Figure 3C:
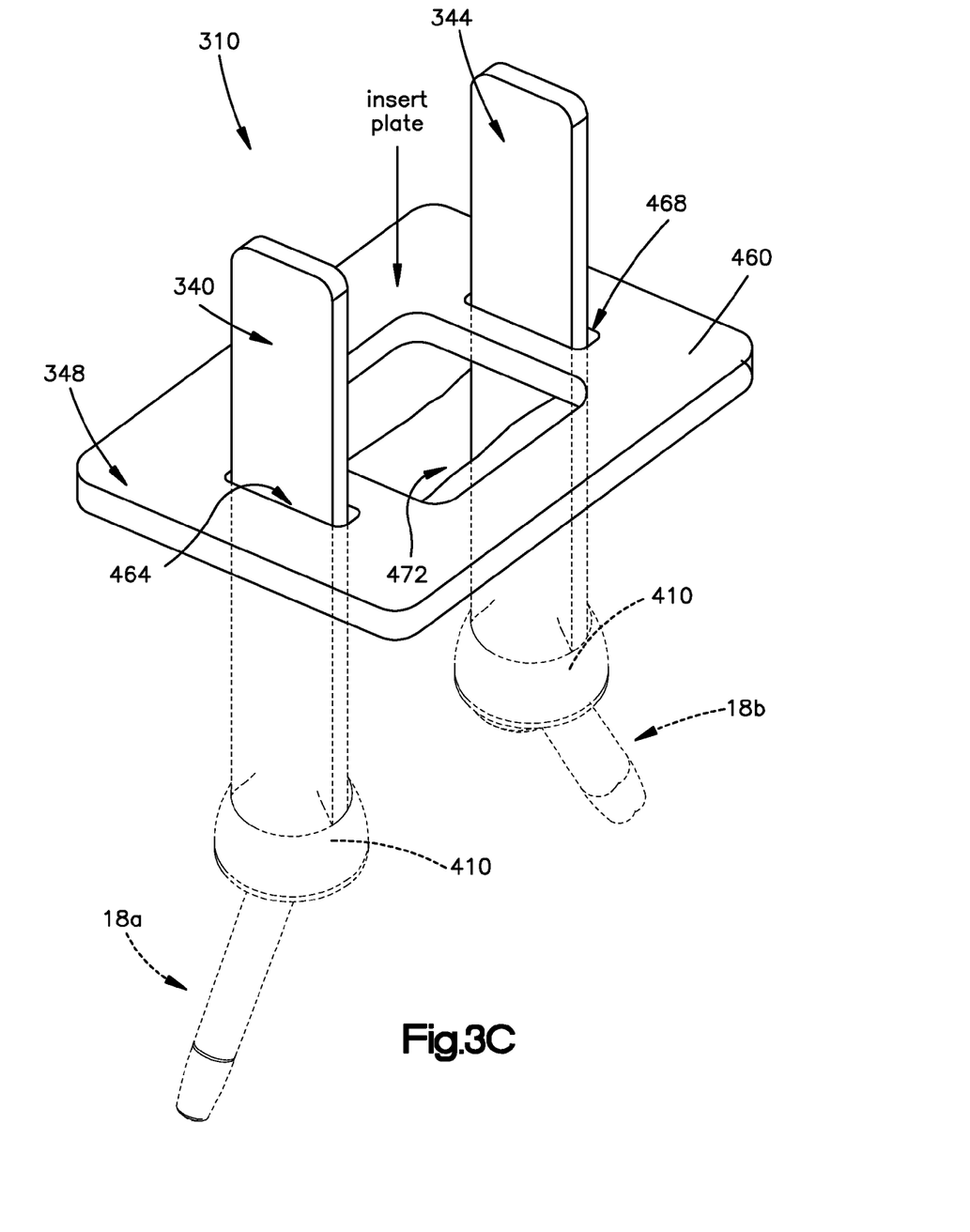
FIG. 3C is a perspective view of the spreader system shown in FIG. 3B, with a holder plate coupled to the first and second posts to thereby fix the first and second posts relative to each other.

In another embodiment and in reference to FIGS. 3A-3C, a spreader system configured as a retractor system 310 can include a first retractor post 340 configured to be coupled to the head 22 of the first bone fixation element 18a, a second retractor post 344 configured to be coupled to the head 22 of the second bone fixation element 18b, and a spreader device configured as a holder plate 348. The holder plate 348 is configured to couple to the first and second retractor posts 340 and 344 such that the holder plate 348 can fix the position of the first and second retractor posts 340 and 344 relative to each other. The first and second retractor posts 340 and 344 are configured to couple to the heads 22 of the first and second bone fixation elements 18a and 18b such that the first and second retractor posts 340 and 344 are polyaxially pivotal relative to the heads 22 of the first and second bone fixation elements 18a and 18b, respectively.

The first and second retractor posts 340 and 344 are similar to the first and second posts 40 and 44 shown in FIGS. 2A and 2B and include like structure unless otherwise described. Furthermore, the first and second retractor posts 340 and 344 function in a similar manner as the posts 40 and 44 unless otherwise described. For example, like the posts 40 and 44, the first and second retractor posts 340 and 344 are configured to couple to the heads 22 of the first and second bone fixation elements 18a and 18b such that the first and second retractor posts 340 and 344 are polyaxially pivotable relative to the heads 22.

As shown in FIGS. 3A-3C, the first and second retractor posts 340 and 344 each includes a post body 400 that is elongate along respective first and second directions and defines a proximal end P and a distal end D that is spaced from the proximal end P along the respective first and second directions. The post body 400 includes a retracting member 404 that defines opposed substantially flat surfaces 408, and a coupling member 410 that extends from a distal end of the retracting member 404. The coupling member 410 is identical to the coupling member 210 of the first retractor post 40 and functions in an identical manner. The retracting member 404 is configured to spread tissue when the posts 340 and 344 are moved away from each other.

As shown in FIG. 3C, the holder plate 348 includes a plate body 460 and defines a first aperture 464 that extends through body 460 along a third direction, a second aperture 468 that also extends through the body 460 along the third direction, and an access window 472 that extends through the body 460 along the third direction and between the first and second apertures 464 and 468. The first and second apertures 464 and 468 are elongate slots and are configured to receive the retracting members 404 of the first and second retractor posts 340 and 344, respectively such that the holder plate 348 fixes the first and second retractor posts 340 and 344 relative to each other when the retracting members 404 are received within the slots.

The access window 472 can be sized so as to provide a surgical workspace or access path to a target surgical location.

The access window 472 can be any size as desired. Moreover, the system 310 can be provided with a plurality of holder plates 348 each plate having an access window 472 of a different size.

In operation, the first bone fixation element 18a can be attached to the first bone part 14a and the second bone fixation element 18b can be attached to the second bone part 14b. The first and second retractor posts 340 and 344 can then be moved through tissue and toward the heads 22 of the first and second bone fixation elements 18a and 18b. Once the distal ends of the first and second retractor posts 340 and 344 contact the heads 22, further movement toward the heads 22 will cause the expandable members to expand and the heads 22 to be received within the sockets. When the heads 22 are received within the sockets the expandable members will contract to thereby apply axial and radial loads to the surfaces 19 of the heads 22 and subsequently couple the retractor posts 340 and 344 to the bone fixation elements 18a and 18b. In this way, the retractor posts 340 and 344 can be said to be pop-on or snap-on coupleable. After the retractor posts 340 and 344 are coupled to the bone fixation elements 18a and 18b, the retractor posts 340 and 344 can be moved to a desired position and the holder plate 348 can be coupled to the posts 340 and 344 to thereby fix the relative position of the posts 340 and 344. That is, the posts 340 and 344 can be inserted through the first and second apertures 464 and 468 of the holder plate 348 to thereby spread and retain the tissue in the spread position. After the surgical procedure has been performed, the retractor system 310 can be removed by moving the system 310 away from the heads 22. In particular, the holder plate 348 can be removed and subsequently the posts 340 and 344 can be removed. As the force away from the heads 22 is increased, the expandable members will once again expand to thereby allow the heads 22 to disengage from the sockets.

While the foregoing description and drawings represent the preferred embodiments of the present invention, it will be understood that various additions, modifications, combinations and/or substitutions may be made therein without departing from the spirit and scope of the invention as defined in the accompanying claims. In particular, it will be clear to those skilled in the art that the invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components, which are particularly adapted to specific environments and operative requirements without departing from the principles of the invention. In addition, features described herein may be used singularly or in combination with other features. For example, features described in connection with one embodiment may be used and/or interchanged with features described in another embodiment. The presently disclosed embodiments are therefore to be considered in all respects as illustrative and not restrictive, the scope of the invention being indicated by the appended claims, and not limited to the foregoing description.

It will be appreciated by those skilled in the art that various modifications and alterations of the invention can be made without departing from the broad scope of the appended claims. Some of these have been discussed above and others will be apparent to those skilled in the art.

What is claimed:

1. A spreader system comprising:
    a first post configured to be coupled to a first bone fixation element that is attached to a first bone part, the first post including a first post body that is elongate along a first direction and defines a proximal end and a distal end spaced from the proximal end along the first direction, the first post further including a first socket that extends into the distal end of the first post body and a first expandable member disposed within the first socket such that as the first socket receives a head of the first bone fixation element the first expandable member expands to permit the first socket to receive the head, and after the first socket has received the head the first expandable member contracts to thereby couple the first bone fixation element to the first post such that the first post is poly-axially pivotable relative to the head of the first bone fixation element; and
    a second post configured to be coupled to a second bone fixation element that is attached to a second bone part, wherein at least one of the first post and second post is configured to move relative to the other after the first and second posts have been coupled to the first and second bone fixation elements, respectively.

2. The spreader system of claim 1, wherein the second post includes a second post body that is elongate along a second direction and defines a proximal end and a distal end spaced from the proximal end along the second direction, the second post further including a second socket that extends into the distal end of the second post body and a second expandable member disposed within the second socket such that as the second socket receives a head of the second bone fixation element the second expandable member expands to permit the second socket to receive the head, and after the second socket has received the head the second expandable member contracts to thereby couple the second bone fixation element to the second post such that the second post is poly-axially pivotable relative to the head of the second bone fixation element.

3. The spreader system of claim 2, wherein the first post body and the second post body each include a retracting member that is elongate along the first and second directions respectively, the retracting members being configured to spread tissue when the first and second posts pivot about the first and second bone fixation elements.

4. The spreader system of claim 3, further comprising a holder plate that defines a first aperture configured to receive the retracting member of the first post body, a second aperture configured to receive the retracting member of the second post body and an access window that extends through holder plate between the first and second apertures, wherein the holder plate is configured to fix the first and second posts relative to each other when the retracting members are received by the first and second apertures.

5. The spreader system of claim 2, further comprising a distractor device having a frame that includes a first arm, a second arm, and a connecting member that couples the first arm to the second arm such that at least one of the first and second arms is configured to move relative to the other along the connecting bar, wherein the first arm is configured to couple to the first post and the second arm is configured to couple to the second post such that as the at least one of the first and second arms is moved relative to the other, at least one of the first and second posts is moved relative to the other.

6. The spreader system of claim 1, wherein the first post body includes an internal surface that defines the first socket and an opening disposed at the distal end of the first post body.

7. The spreader system of claim 6, wherein the first internal surface is substantially spherical.

8. The spreader system of claim 6, wherein the first post body includes a circumferential recess that extends radially into the internal surface proximate to the opening, the first expandable member being at least partially disposed within the circumferential recess.

9. The spreader system of claim 1, wherein the first expandable member is a canted-coil spring.

10. The spreader system of claim 1, wherein the expandable member is configured to provide at least a radial load to the head of the first bone fixation element.

11. The spreader system of claim 1, wherein the expandable member defines an internal diameter that expands so as to be substantially equal to a maximum diameter of the head of the first bone fixation element as the socket receives the head of the first bone fixation element.

12. The spreader system of claim 11, wherein the first post is polyaxially pivotable relative to the head of the first bone fixation element in multiple planes when the first post is coupled to the first bone fixation element.

13. The spreader system of claim 11, wherein the first post is configured to rotate about a central axis of the first post when the first post is coupled to the first bone fixation element.

* * * * *